(12) United States Patent
Ito et al.

(10) Patent No.: US 6,312,918 B1
(45) Date of Patent: Nov. 6, 2001

(54) **EXAMINATION METHOD OF INFECTION WITH *HELICOBACTER PYLORI***

(75) Inventors: Masaharu Ito, Ibaraki-ken; Kunitoshi Matsunobu, Kanagawa-ken; Masanori Uono, Kanagawa-ken; Susumu Kanemaki, Kanagawa-ken; Kyoichi Kobashi, Toyama-ken, all of (JP)

(73) Assignees: Gastec Corporation, Kanagawa-ken; Eisai Co., Ltd., Tokyo, both of (JP)

( * ) Notice: Subject to any disclaimer, the term of this patent is extended or adjusted under 35 U.S.C. 154(b) by 0 days.

(21) Appl. No.: 08/423,865

(22) Filed: Apr. 18, 1995

(30) Foreign Application Priority Data

Apr. 27, 1994 (JP) .................................................... 6-089515

(51) Int. Cl.⁷ ........................................................ C12Q 1/04
(52) U.S. Cl. ................................................ 435/34; 435/12
(58) Field of Search ................................... 435/34, 10, 12

(56) References Cited

U.S. PATENT DOCUMENTS

| | | | |
|---|---|---|---|
| 4,947,861 | * | 8/1990 | Hamilton .............................. 128/719 |
| 5,314,804 | * | 5/1994 | Boguslaski et al. ................... 435/12 |
| 5,409,903 | * | 4/1995 | Polak et al. ............................ 514/23 |

OTHER PUBLICATIONS

Mertz H., Diagnosis of *Campylobacter pylor* Gastritis, Digestive Diseases and Sciences, 36(1) 1–4, Jan. 1991.*

Koletzko, S., Isotope–Selective Non–Despersive Infrared Spectrometry for Detection of *Helicobacter pylori* Infection with 13C–Urea Breath Test, Lancet vol. 345, 961–962, Apr. 1995.*

"Unidentified Curved Bacilli in the Stomach of Pateints with Gastritis and Peptic Ulceration," The Lancet, Jun. 16, 1994, vol. I, No. 8390, pp. 1311–1314, London.

* cited by examiner

*Primary Examiner*—Ralph Gitomer
(74) *Attorney, Agent, or Firm*—Arent Fox Kintner Plotkin & Kahn, PLLC

(57) ABSTRACT

There are described a simple examination method of infection with *Helicobacter pylori* possibly presenting in a gastric mucosa, and a device therefor. The examination is conducted by collecting gas in gastric cavity, and measuring mainly ammonia and additionally organic amines which are generated due to activities of the bacilli. The measurement is carried out by leading the gas in gastric cavity into oral cavity by vomiting-reflex, and sucking the gas by a metering suction pump through a gas detection tube to read-out a length of color-changed area in the gas detection tube.

5 Claims, 6 Drawing Sheets

○ : NH4Cl (100μg/ml, 25°C)
● : NH4Cl (100μg/ml, 37°C)
△ : NH4Cl (200μg/ml, 25°C)
▲ : NH4Cl (200μg/ml, 37°C)
◇ : NH4Cl (400μg/ml, 25°C)
◆ : NH4Cl (400μg/ml, 37°C)
□ : NH4Cl (800μg/ml, 25°C)
■ : NH4Cl (800μg/ml, 37°C)
× : NH4Cl (1600μg/ml, 25°C)
∗ : NH4Cl (1600μg/ml, 37°C)

○ : No. 1 (NH$_4$Cl, 0μg/ml)
○ : No. 2 (NH$_4$Cl, 0μg/ml)
○ : No. 3 (NH$_4$Cl, 0μg/ml)
△ : No. 1 (NH$_4$Cl, 800μg/ml)
△ : No. 2 (NH$_4$Cl, 800μg/ml)
△ : No. 3 (NH$_4$Cl, 800μg/ml)
■ : No. 1 (NH$_4$Cl, 1600μg/ml)
■ : No. 2 (NH$_4$Cl, 1600μg/ml)
■ : No. 3 (NH$_4$Cl, 1600μg/ml)

□ : No. 1 (NH4Cl, 0μg/ml)
□ : No. 2 (NH4Cl, 0μg/ml)
□ : No. 3 (NH4Cl, 0μg/ml)
■ : No. 1 (NH4Cl, 0μg/ml), infected with H.p.
■ : No. 2 (NH4Cl, 0μg/ml), infected with H.p.
■ : No. 3 (NH4Cl, 0μg/ml), infected with H.p.

EXAMINATION METHOD OF INFECTION WITH *HELICOBACTER PYLORI*

BACKGROUND OF THE INVENTION

1. Field of the Invention

The present invention relates to a simple examination method of infection with *Helicobacter pylori* (hereinafter may also be abbreviated as "*H.p.*") which is a bacillus and may present in gastric mucosa, and a device therefor. According to the invention, the information on *H.p.*-infection and the activity of *H.p.* at the time of examination can be easily obtained.

2. Related Arts

Because of the strongly acidic environment of the inside of the stomach, the gastric cavity had been considered unsuitable for the survival of bacilli since old times; however, about 100 years ago, the existence of spiral bacillus was observed and reported. The bacilli were formally discovered in the second half of the 1970's. In 1983, the bacilli were firstly isolated from gastric mucosa by Waren et al., and was named at first as "*Campylobacter pyloridis*, because it morphologically and biologically resembled Campylobacter which is one or *Salmonella enteritidis*, in addition to the fact that it was isolated from gastric antral mucosa in the vicinity of the pylorus. Later, the name was once changed to *Campylobacter pylori*. The genetic name has been changed to "Helicobacter" based on its form, since the difference from Campylobacter became clear in 1989.

Continuous effort has been made investigating the correlation between *H.p.* and diseases of the upper alimentary tract even since the bacilli were isolated at a high rate by Marshall et al. From patients with gastric ulcer, duodenal ulcer or chronic gastritis in 1984, and the association between the presence of the bacilli and these diseases has been reported ["The lancet", No. 8390, pages 1311–1314 (June 1984)].

According to the subsequent study results, although the correlation has not been proved, *H.p.* are regarded as an important factor in the etiology of cancer of the stomach; therefore, the diagnosis of *H.p.*-infection has an important clinical significance to the treatment for the aforesaid diseases.

At the present time, such methods of examining *H.p.* as a microscopic examination method on gastric mucosa, a cultivation method of gastric mucosa tissue, and a rapid urease test on gastric mucosa tissue have been in the art, but all of the conventional methods need endoscopy which requires advanced technical skill or expertise and is too heavy a burden for patients; therefore, the clinical application of these methods is limited.

On the other hand, a method, which is now under consideration, for measuring anti-*H.p.* antibodies in blood or sputum cannot be applied for obtaining information on the present state of *H.p.*-infection, because of the time lag between *H.p.*-infection and appearance of the antibodies, or between *H.p.*-elimination and disappearance of the antibodies.

There is a $^{13}$C-breath test as the method for obtaining informations on the present state of *H.p.*-infection without causing pain to the patients, but the clinical application thereof is also limited, because of the necessity of a radio-isotope in combination with a large-sized and expensive apparatus, in addition to the inability of speeding up the operation of the apparatus in connection with the transportation of the specimen.

We have just found U.S. Pat. No. 4,947,861 (issued Aug. 14, 1990) disclosing a diagnosis of *H.p.* infection. In the patent specification (columns 2–4), Hamilton teaches a fact that ammonia could not be detected in expired alveolar air with a conventional apparatus, although the detection has been made based on theory that if urea is administered to a person infected with *H.p.*, at least some portion of ammonia generated by the activity of *H.p.* is absorbed into the blood stream, passes through the liver without being broken down there, and is delivered to expired air at the alveoli of the lungs, but can be detected with the conventional apparatus, if a breath sample is treated by a desiccant material such as sodium hydroxide to absorb therein $H_2O$ and $CO_2$ in the sample breath and collect the dried breath, prior to the detection. however, he does not disclose any actual Example on diagnosis of *H.p.*-infection. We think this means that even if ammonia in the breath sample can be detected, an application of the method for the actual diagnosis is quite difficult or impossible from the view point of sensitivity, since almost all part of ammonia absorbed into the blood stream will be broken down by the liver and only a trace amount thereof shall appear in the breath sample, as stated also by him (line 24 in column 3).

OBJECT AND SUMMARY OF THE INVENTION

As described above, conventional methods of examining *H.p.*-infection have both advantages and disadvantages.

Therefore, a principal object of the invention is to provide a simple examination method of infection with *H.p.* without causing pain to the patients, wherein the method does not need a large-sized expensive apparatus, and informations on *H.p.*-infection and activity of *H.p.* can be obtained in situ.

A secondary but important object of the invention is to provide a simple device for examining *H.p.*

It has been estimated that *H.p.* produce alkaline ammonia for neutralizing the gastric acid to make possible their survival in the strong acidic gastric cavity. Thus, on the basis of the recognition that *H.p.* have a high unit of urease which is specific to the production of ammonia and the produced ammonia shall present in high concentrations in the intragastric gas and gastric juice of *H.p.*-infected patients, the inventors have energetically studied and investigated to find out that there is a close correlation between the intragastric ammonia concentration and *H.p.*-infection, and by measuring the concentration, information on the present activity of *H.p.* at the time of examination can be obtained, so that the invention has been established.

The simple examination method of infection with *H.p.* according to the invention, therefore, comprises collecting a given amount, of gas in the gastric cavity, and then measuring primarily the ammonia and secondarily organic amines therein.

A number of ways have been presented in order to collect the intragastric gas; one is a method of collecting the gas directly by use of a cannula. However, the method cannot be conducted to collect the intragastric gas without causing pain to the subjects.

For the purpose of collecting the intragastric gas, it has now been found to be advantageous to lead the gas to the oral cavity with the aid of vomiting-reflexive belching, so-called "eructation" caused by the stimulation, for example, of the throat or the larynx.

It is preferable to administer an alkaline agent, urea preparation or hot water prior to the collection of the intragastric gas. The alkaline agent is used to facilitate the gasification of ammonia and organic amines, such as methyl amine, by reacting it with gastric acid. The urea preparation is used to produce ammonia in amounts correspond to the degree of H.p.-infection or the state of activity of H.p. by reacting it as substrate with urease which H.p. has, and the hot water (40–50° C. ) is used to increase the efficiency of gasification of ammonia by raising temperature in the gastric cavity.

Examples of the alkaline agents include sodium bicarbonate, precipitated calcium carbonate, magnesium oxide, magnesium carbonate, magnesium hydroxide, magnesium silicate, magnesium aluminate, aluminum silicate, aluminum hydroxide, magnesium meta-silicate aluminate, dimagnesium silicate aluminate, a co-precipitated composition comprising aluminum hydroxide/magnesium carbonate/calcium carbonate, and the like.

The gas collected from the gastric cavity is led to a sensor to measure total amount or ammonia and organic amines, because of that the gas consists primarily of ammonia, but organic amine gases shall possibly present therein, and the sensor detects the amines in addition to ammonia. Examples of such sensors include a gas detection tube (gas-detecting reagents in the tube changes in color by contacting with ammonia and organic amines), a pH indicator, a pH-meter, an oxidation-reduction potential electrode, and the like.

Among the above, the gas detection tube is particularly preferred because it is simple in structure and when is used in combination with a conventional metering suction pump, the intragastric gas collected in the oral cavity through the gastric cavity with the aid of belching can be directly red into the gas detection tube, thereby permitting the measurement of ammonia and organic amines.

The gas detection tube is a thin or slender glass tube packed with a conventional dried gas-detecting reagents comprising sulfuric acid and Cresol Red supported on silica sand as a carrier, which has been known and commercially available in the market.

As described above, the H.p.-examining device according to the present, invention comprises a metering suction pump, a gas detection tube, and a member for stimulating the throat or larynx to cause a vomiting reflex.

It is preferable that front end of the the metering suction pump and one end of the gas detection tube is connected through a flexible conduit. since if the flexible conduit is employed, subjects can easily manipulate the pump by bending the conduit part while holding the tube in the vicinity of its free end in the mouth. Further, a round tip member should be used for stimulating the throat or laryngeal part of pharynx, whereby the device can be manipulated without damaging the inside of the mouth.

DETAILED DESCRIPTION OF THE PREFERRED EMBODIMENT

The invention will now be further explained in more detail and concretely with reference to Preliminary Examples and Actual Measurements.

PRELIMINARY EXAMPLE 1

Investigation on Quantification of Ammonia
(1) Correlation Between Concentrations of Ammonium Chloride Solution and Gaseous Ammonia To a 0.01N-HCl solution was added $NH_4Cl$ to prepare solutions containing $NH_4Cl$ in respective concentrations of 100, 200, 400, 800, and 1600 μg/ml. To 40 ml of each solution (in a 1-litre volume polyethylene bottle) was added MgO in an amount of 0, 0.05, 0.1, 0.3, 0.6, and 1.0 g, respectively. Immediately after shaking for 1 minute, gaseous ammonia concentration in each bottle was determined by measurement with a gas detection tube mounted on a metering suction pump (suction amount: 100 mL) at both of room temperature (25° C.) and 37° C. The measurement at 37° C. was carried out in a thermostat. The pH of solution was also measured by a pH meter.

Figure 1:
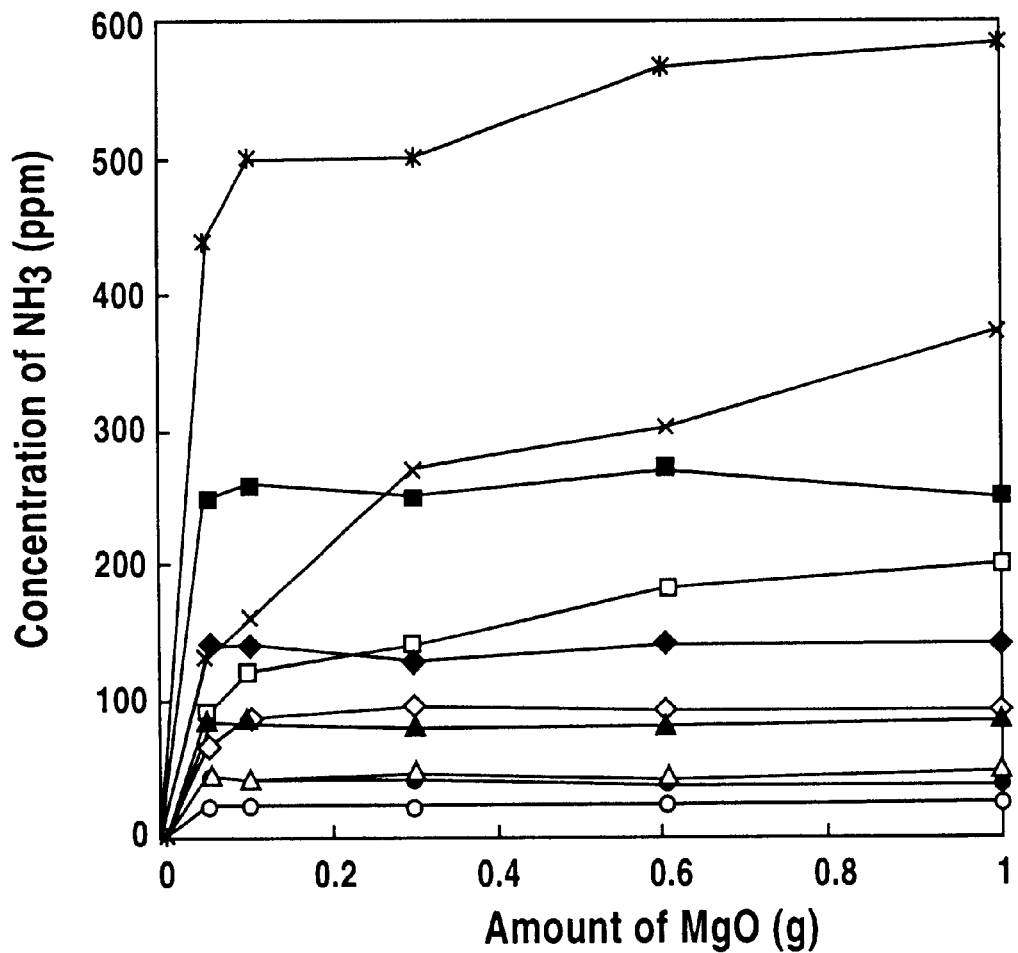
FIG. 1 is a graph showing in vitro test results obtained by measuring concentration of ammonia generated when magnesium oxide is added to an ammonium chloride/HCl solution.

Results are shown in following Table 1 and FIG. 1.

TABLE 1

| MgO (g) | Item of measurement | | Concentration of $NH_4Cl$ (μg/ml) | | | | |
|---|---|---|---|---|---|---|---|
| | | | 100 | 200 | 400 | 800 | 1600 |
| 0 | $NH_3$ (ppm) | 25° C. | 0 | 0 | 0 | 0 | 0 |
| | | 37° C. | 0 | 0 | 0 | 0 | 1 |
| | pH | 25° C. | 2.09 | 2.09 | 2.08 | 2.12 | 2.13 |
| 0.05 | $NH_3$ (ppm) | 25° C. | 21 | 42 | 65 | 90 | 130 |
| | | 37° C. | 42 | 85 | 140 | 250 | 440 |
| | pH | 25° C. | 10.38 | 10.30 | 10.30 | 10.23 | 9.96 |
| 0.1 | $NH_3$ (ppm) | 25° C. | 22 | 40 | 85 | 120 | 160 |
| | | 37° C. | 38 | 85 | 140 | 260 | 500 |
| | pH | 25° C. | 10.32 | 10.25 | 10.30 | 10.25 | 10.13 |
| 0.3 | $NH_3$ (ppm) | 25° C. | 20 | 44 | 95 | 140 | 270 |
| | | 37° C. | 40 | 80 | 130 | 250 | 500 |
| | pH | 25° C. | 10.28 | 10.21 | 10.20 | 10.20 | 10.07 |
| 0.6 | $NH_3$ (ppm) | 25° C. | 23 | 40 | 90 | 180 | 300 |
| | | 37° C. | 36 | 80 | 140 | 270 | 560 |
| | pH | 25° C. | 10.30 | 10.20 | 10.20 | 10.17 | 10.07 |
| 1.0 | $NH_3$ (ppm) | 25° C. | 22 | 42 | 90 | 200 | 370 |
| | | 37° C. | 36 | 85 | 140 | 250 | 580 |
| | pH | 25° C. | 10.21 | 10.20 | 10.17 | 10.18 | 10.07 |

Followings have been found from the results shown in Table 1 and FIG. 1.

(a) The gasification of ammonia is affected by environmental temperature. A higher concentration of ammonia is detected at 37° C. than at 25° C.

(b) Under the temperature condition of 37° C., ammonia gas generated by the addition of 0.6 g of MgO reaches an equilibrium in concentration; and (c) There is a close correlation between the $NH_4Cl$ concentration arid concentration of ammonia gas to be generated.

Based on these facts, it is concluded that the ammonia concentration in a solution can be easily determined by measuring ammonia gasified under given conditions.

(2) Comparison of $NH_4Cl$ Solution with Human Gastric Juice

In four 1-litre volume polyethylene bottles, the following respective solutions were charged:

A: Gastric juice (40 ml)

B: $NH_4Cl$ Solution (40 ml, 160µg of $NH_4Cl$/ml in 0.008N-HCl)

C: Gastric juice (10 ml, collected after administration of 0.6 g MgO)

D: $NH_4Cl$ solution (10 ml, 160 µg of $NH_4Cl$/ml in 0.008N-HCl)

The concentration of gaseous ammonia and pH of the solution in each bottle were measured by a method as described in Item (1).

Results are shown in following Table 2. When comparing human gastric juice with the $NH_4Cl$ solution at measuring temperature of 20° C. and 37° C., it is noticed that there is a close correlation between them; therefore, it has been found that the ammonia concentration of gastric juice can be easily determined by gasifying ammonia dissolved in gastric juice under the given conditions.

TABLE 2

| Solution | | | | Add no MgO | | Add MgO (0.6 g) | |
|---|---|---|---|---|---|---|---|
| Kind | pH | $NH_3$ (µ g/ml) | Temp. (° C.) | $NH_3$ gas (ppm) | pH | $NH_3$ gas (ppm) | pH |
| A | 2.28 | 49 | 25 | 0 | 2.28 | 38 | 10.22 |
|   |      |    | 37 | 0 |      | 50 |       |
| B | 2.21 | 50 | 25 | 0 | 2.21 | 40 | 10.15 |
|   |      |    | 37 | 0 |      | 64 |       |
| C | 9.50 | 52 | 25 | 18 | 9.50 | 35 | 10.03 |
|   |      |    | 37 | 45 |      | 50 |       |
| D | 2.21 | 50 | 25 | 0 | 2.21 | 32 | 10.33 |
|   |      |    | 37 | 0 |      | 60 |       |

Preliminary Example 2

Investigation on Healthy Individuals, Dose Dependency

Following experiments were conducted on healthy individuals who had no lesion in their digestive systems.

Figure 2:
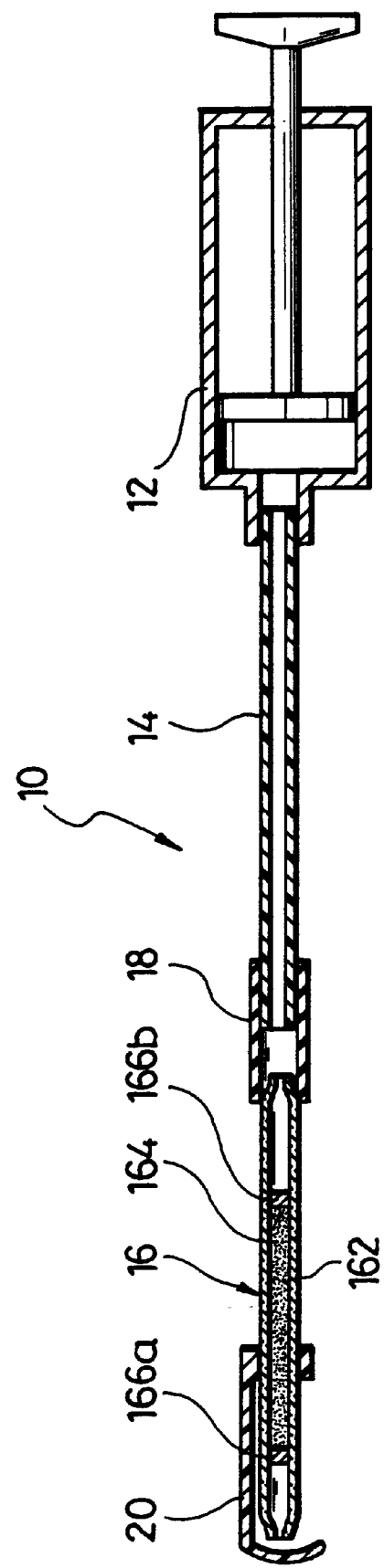
FIG. 2 is a longitudinal section of a device according to the invention for examining *Helicobacter pylori*.

In these experiments, concentration of gaseous ammonia in the oral cavity was determined by using a device 10 shown in FIG. 2. The device comprises a metering suction pump 12 having a conventional structure, a flexible conduit 14 fitted into front suction end of the suction pump, a conventional gas detection tube 16, a sleeve 18 connecting one end of the gas detection tube with free end of the flexible conduit 14, and a throat- or a larynx-stimulating member 20 attached to the gas detection tube in the vicinity of its free end. The suction volume of pump 12 was 100 ml; however, it may be considered to more less, for example, 50 ml, because the suction of the gas in the oral cavity is carried out in a way that the vicinity of its free end of the gas detection tube is held with one's mouth shut.

In the gas collecting device of the present invention, although it is not absolutely necessary to provide the device with the flexible conduit in between the suction pump and the gas detection tube, the conduit is useful in facilitating aspiration of the gas in the oral cavity. Material of the conduit may be of a synthetic resin such as polyethylene, polystyrene, polypropylene or the like. The gas detection tube 16 is provided with a narrow tube 162 made of transparent glass, in which a dried gas-detecting reagents 164 comprising sulfuric acid and Cresol Red absorbed on silica sand as a carrier is packed in between air-permeable partitions or packings 166a, 166b. The gas-detecting reagents will change in color, when they contact with ammonia and/or organic amines. Determination of the particular gas concentration of the current passing through the tube can be achieved by measurement of the length of color-changed area or section with an aid of a scale on the gas detection tube. Nonused gas detection tube has been melt-sealed at its both ends, and the tube should be broken at its ends in order for use, as shown in FIG. 2. From viewpoint of feeling in touch, the throat-larynx-stimulating member 20 is preferably prepared by polystyrene or polyethylene. The shape or the member 20 can be optionally selected, but a round-shaped structure at its tip is preferably employed because such a round-shaped member prevents the inside of the oral cavity from scratching. In addition, the gas detection tube in itself may be designed not to touch the oral mucosa when the throat or larynx is stimulated.

The experiments were conducted along a following outline.

After the teeth were brushed well and the oral cavity was rinsed out by gargles, the gaseous ammonia concentration in the oral cavity of a hungry subject in early morning was determined 3 times at an interval of 3 minutes by using the device shown in FIG. 2. Immediately after the administration of 0.6 g MgO in 20 ml water (40° C.) to the standing subject, 40 ml (40° C.) of respective $NH_4Cl$ solution (0, 800 or 1600µg/ml) were administered, followed by the administration of 40 ml (40° C.) hot water already used for rinsing out the oral cavity. After the full gargling with 100–200 ml water, the gargling water was discarded.

The throat or the larynx was then stimulated with the tip of the device shown in FIG. 2, so that a vomiting reflex could be given 3 times to measure the ammonia gas concentration in the oral cavity after lapsed 5, 10, 15, 20 and 30 minutes. The procedure of measurement is set forth in following Table 3.

TABLE 3

Teeth-brushing and gargling
↓
−9 min. (1st preliminary measurement)
↓
−6 min. (2nd preliminary measurement)
↓
−3 min. (3rd preliminary measurement)
↓
0 min. (administration of MgO and NH4Cl)
↓
5 min. (1st measurement)
↓
10 min. (2nd measurement)
↓
15 min. (3rd measurement)
↓
20 min. (4th measurement)
↓
30 min. (5th measurement)

Figure 3:
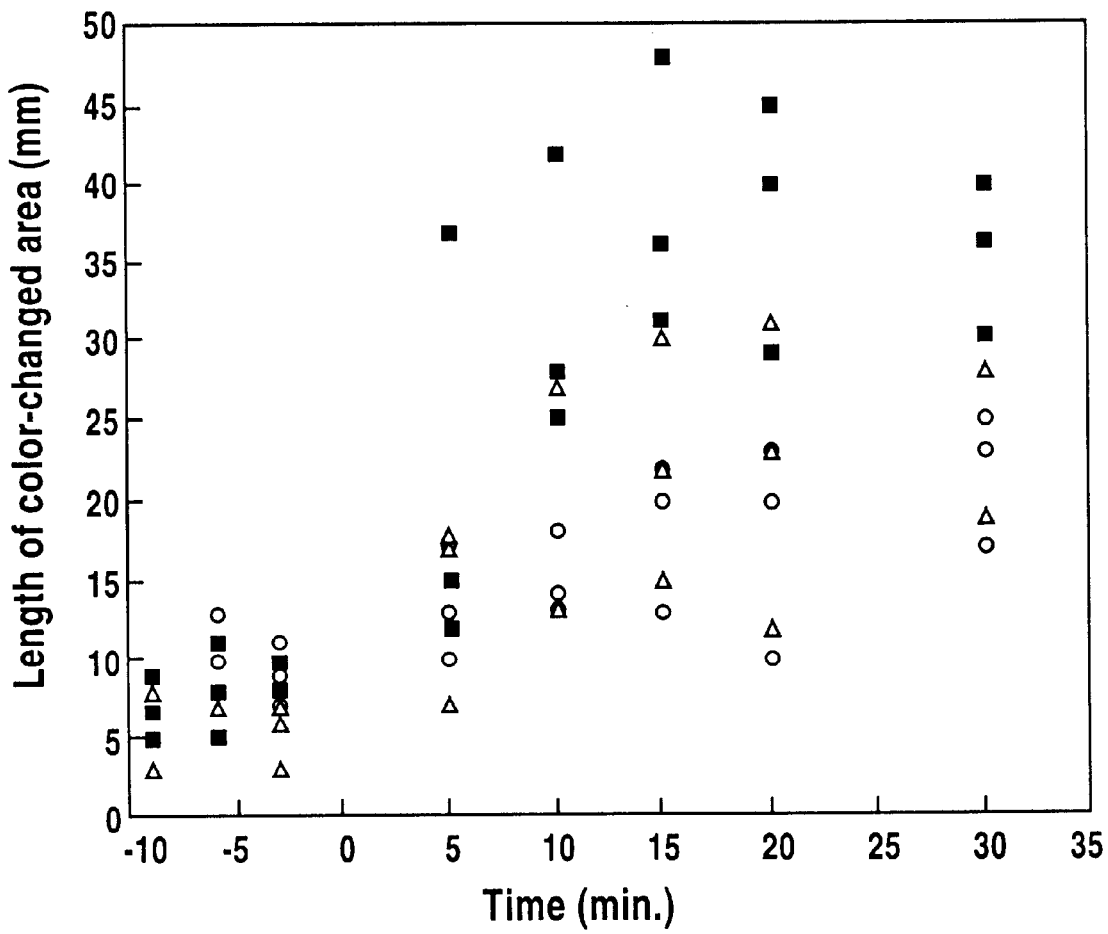
FIG. 3 is a graph showing a transition in ammonia concentration of the gas in the oral cavity for 3 healthy individuals who were administered magnesium oxide (0.6 g) and ammonium chloride (0, 800 or 1600 μg/ml), wherein the concentration was determined by the method according to the invention before and after the vomiting-reflex.

Results are shown in following Table 4 and FIG. 3. As apparently seen therefrom, the $NH_3$ concentration to be detected increases, as the loading amount of $NH_4Cl$ increases, and a significant difference (p<5) was recognized in the respective passage lapsed for 10, 15, 20 and 30 minutes from the administration between the control group (administered $NH_4Cl$: 0 μg/ml) and the test group (administered $NH_4Cl$: 1600 μg/ml).

TABLE 4

| $NH_4Cl$ (μ g/ml) | Subject (No.) | Time (min.) | | | | | | | |
|---|---|---|---|---|---|---|---|---|---|
| | | −9 | −6 | −3 | 5 | 10 | 15 | 20 | 30 |
| 0 | 1 | 5 | 5 | 7 | 10 | 13 | 13 | 10 | 17 |
| | 2 | 9 | 10 | 9 | 13 | 14 | 20 | 20 | 23 |
| | 3 | 7 | 13 | 11 | 17 | 18 | 22 | 23 | 25 |
| | Mean | 7.0 | 9.3 | 9.0 | 13.3 | 15.0 | 18.3 | 17.7 | 21.7 |
| 800 | 1 | 3 | — | 3 | 7 | 13 | 15 | 12 | 19 |
| | 2 | 7 | — | 6 | 17 | 27 | 22 | 23 | 28 |
| | 3 | 8 | 7 | 7 | 18 | 25 | 30 | 31 | 30 |
| | Mean | 6.0 | — | 5.3 | 14.0 | 21.7 | 22.3 | 22.0 | 25.7 |
| 1600 | 1 | 5 | 5 | — | 15 | 28 | 31 | 29 | 36 |
| | 2 | 9 | 11 | 10 | 12 | 25 | 48 | 45 | 40 |
| | 3 | 7 | 8 | 8 | 37 | 42 | 36 | 40 | 30 |
| | Mean | 7.0 | 8.0 | 9.0 | 21.3 | 31.7 | 38.3 | 38.0 | 35.3 |

Note:
In Table 4, numerals are given by length (mm) of color-changed area in gas detection tube Example 1

Investigation on Patients Infected with *H.p.*

Three individuals definitely diagnosed as patients infected with *H.p.* (they are positive by both of a *H.p.* antibody measuring test and tissue cultivation test) were examined for ammonia concentration of the gas in their oral cavity under conditions same as described in Preliminary Example 2 ($NH_4Cl$ : 0 μg/m).

The results are shown in following Table 5.

TABLE 5

| Patient | Time (min.) | | | | | | | |
|---|---|---|---|---|---|---|---|---|
| | −9 | −6 | −3 | 5 | 10 | 15 | 20 | 30 |
| 1 | 8 | 10 | 9 | 26 | 36 | 44 | 38 | 35 |
| 2 | 10 | 11 | 7 | 26 | 33 | 30 | 29 | 31 |
| 3 | 18 | 20 | 28 | 28 | 37 | 48 | 46 | 40 |
| Mean | 12.0 | 13.7 | 14.7 | 26.7 | 35.3 | 40.7 | 37.7 | 35.3 |

Note:
In Table 5, numerals are given by length (mm) of color-changed area in the gas detection tube Table 5 shows that the values varied widely and the length of color-changed area in the gas detection tube was remarkably scattered in the range of 8 to 28 mm on the patients infected with *H.p.*, before the loading of MgO; however, the colored length was stable and 26 mm or more in all of the measurements after the loading of MgO.

Figure 4:
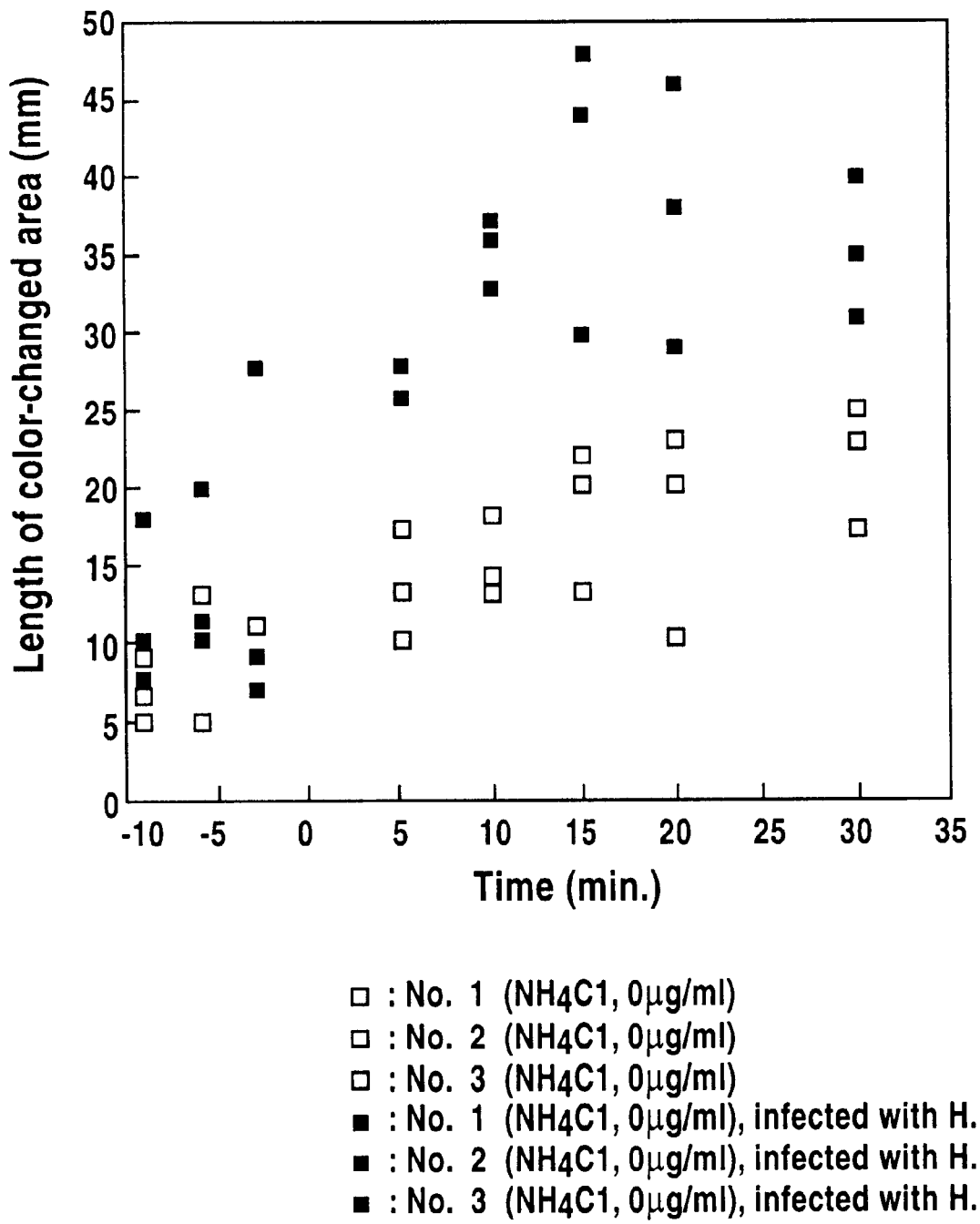
FIG. 4 is a graph showing results checked a transition in ammonia concentration of the gas in the oral cavity for 3 healthy individuals and other 3 individuals infected with *Helicobacter pylori*, wherein the concentration was determined by the method according to the invention before and after the vomitingreflex.

Further, FIG. 4 shows a comparison of the transition of ammonia concentration for healthy individuals (three individuals referred to as Nos. 1, 2 and 3) with those for *H.p.*-infected patients (three individuals referred to as Nos. 4, 5 and 6, but they are same with the patients of Nos. 1, 2 and 3 in Table 5, respectively). A significant difference (p<5) was recognized between the results of the two groups at the time of examination conducted respectively at 5, 10, 15, 20 and 30 minutes after a vomiting reflex. it has been made apparent that higher ammonia concentrations are detected for *H.p.*-infected patients in comparison with those for healthy individuals

EXAMPLE 2

Urea-loading Test

Two subjects were selected (one was a *H.p.*-negative healthy individual and another was a patient definitely diagnosed as infected with *H.p.*).

After the teeth of the subject were fully brushed and the mouth was rinsed out by gargle at an early morning, gas in the oral cavity of the respective hungry subjects was collected by means of the device shown in FIG. 2, thereafter ammonia concentration of the gas was measured at an interval of 3 minutes. All measurements were repeated 3 times. Urea (150 mg) dissolved in water (40 ml, 40° C.) was then administrated to the subject in a standing position, and the mouth was rinsed with water (60 ml) which was also administered. The mouth was again rinsed by gargle with hot water (100–200 ml) which was discarded after use.

The measurement was repeated 4 times at an interval of 5 minutes. The throat or larynx was then stimulated with the tip of the device shown in FIG. 2 so as to give a vomiting-reflex by 3 times.

The measurement was further repeated 4 times at an interval of 5 minutes. The results in Table 6 shows that in *H.p.*-infected patients, all measurements conducted 20 minutes after the loading of urea indicated a high ammonia concentration. in *H.p.*-infected patients, all measurements conducted 20 minutes after a vomiting-reflex also indicated a high ammonia concentration.

TABLE 6

| Time | Healthy person | H.p. Patient |
|---|---|---|
| −9 | 10 | 7 |
| −6 | 8 | 7 |
| −3 | 8 | 10 |
| Loading of urea | — | — |
| 5 | 8 | 36 |
| 10 | 11 | 17 |
| 15 | 11 | 20 |
| 20 | 10 | 15 |
| Vomiting-reflex | — | — |
| 5 | 22 | 48 |
| 10 | 16 | 42 |
| 15 | 16 | 31 |
| 20 | 13 | 32 |

Note: In Table 6, the numerals in the left represent the passage of time (minutes) since the time of urea-loading and the vomiting-reflex, and the others indicate the length (in mm) of color-changed area in the gas detection tube.

Note: fn Table 6, the numerals in the left represent the passage of time (minutes) since the time of urea-loading and the vomiting-reflex, and the others indicate the length (in mm) of color-changed area in the gas detection tube.

Although a transition in ammonia concentration in the oral cavity was examined in each Example given above, a concrete example of the testing method is as follows:

After the teeth of a subject were brushed well and the oral cavity was fully rinsed out by gargle to clean the same, ammonia concentration of the gas in the oral cavity was determined by measurement in 1–5 times at an interval of several minutes. After a vomiting-reflex (including cases given by the administration of an alkali agent, an urea solution or hot water), ammonia concentration inside the oral cavity is again determined by measurement in 1–10 times at an interval of several minutes.

By examining the difference between AUC (area under the curve) values of graphs made by plotting measurements or the mean values of ammonia concentration before and after a vomiting-reflex, the subject is judged as *H.p.*-positive when the difference is large.

For convenience, the judgment may be made according to a single measurement conducted after lapsed several minutes—one hour from a vomiting-reflex.

Embodiment on Improved Larynx-stimulating Member

The larynx-stimulating member 20 as shown in FIG. 2 is not so suitable, since the patient should held the same together with one end of the glass gas detection tube 16, when the gas in the gastric cavity, which is delivered to oral cavity by vomiting-reflex is sucked for the detection of ammonia and organic amines therein and it may strike terror to the patient's heart.

Figure 5:
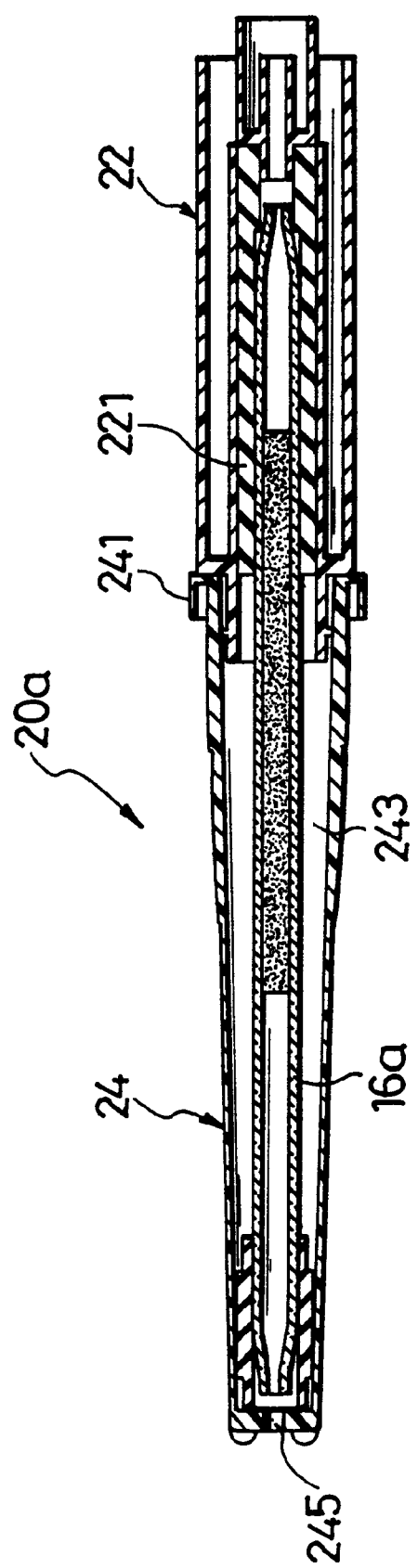
FIG. 5 is a longitudinal section showing another embodiment of larynx-stimulating member.
Figure 6:
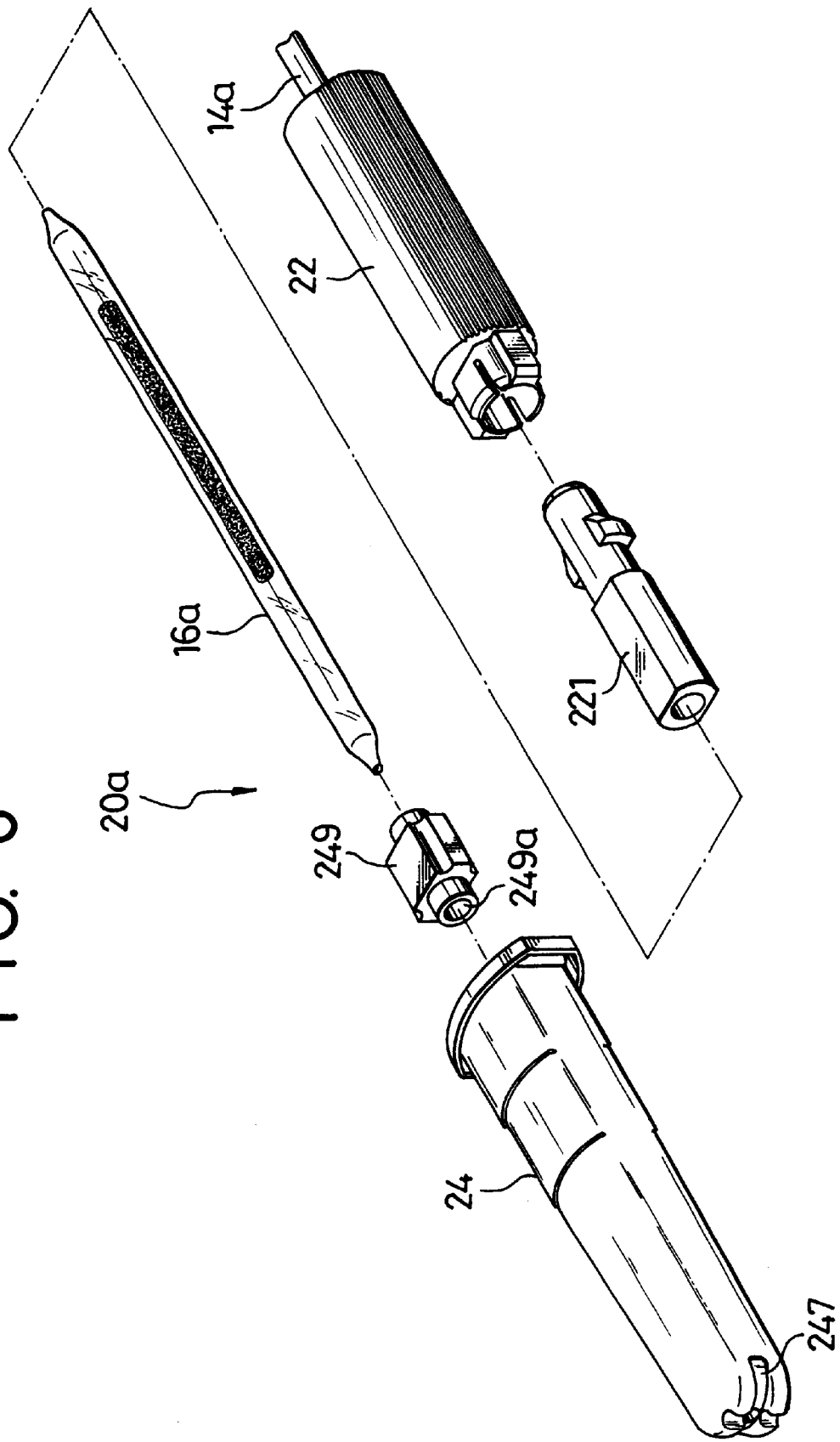
FIG. 6 is an exploded perspective view of the larynx-stimulating member shown in FIG. 5.

Therefore, another larynx-stimulating member 20*a* as shown in FIGS. 5 and 6 was designed. The member 20*a* comprises an adapter 22 and disposable tip member 24 for stimulating the larynx to cause belching. Both of the adapter 22 and disposable tip member 24 are made from synthetic polypropylene resin and can be detachably engaged each other. The disposable tip member 24 has semi-transparency, so that the presence or absence of a glass gas detection tube 16*a* in the space formed by both of the adapter 22 and disposable tip member 24 can be confirmed. The rear end of adapter 22 is fittingly connected to free end of a flexible tube 14*a* as in the member 14 shown in FIG. 2.

In the adapter 22, here is a hollow member 221 made from styrene-butadiene rubber having Shore hardness of 500, which member 221 has a step-like portion on each of inner and outer surface thereof to prevent its sliding movement, when the gas detection tube 16*a* is inserted to securely hold the same at its rear end by the adapter 22. The disposable tip member 24 has an elongational shape in visual appearance and a round rectangular form in section to ensure easy holding the same by mouth shut; a flange 241 at rear end thereof to ensure safety in use and make easy handling for the connection between the disposable tip member 24 and the adapter 22 without touch to the elongated portion of the disposable tip member 24, where the patient holds the same by his mouth shut; a central bore 243 for accommodating a part of the gas detection tube 16*a*; an opening 245 small in diameter and formed at tip-end thereof; and a cross channel 247 formed at outer tip-end surface. The cross channel is convenient to stimulate the larynx. At the portion near end of the the disposable body, a member 249 with a central bore 249*a* is fittingly inserted, which is made from the material same with the hollow rubber member 221 for the adapter 22. When the rubber member 249 had been inserted into the central bore 243 of the disposal tip member 24, front end surface of the rubber member 249 abuts to inner end surface of the disposable tip member 24 to communicate the central bore 249*a* with the opening 245 formed in the disposable tip member 24, and rear portion thereof serves to hold front end of the gas detection tube 16*a*.

As referred to, the glass gas detection tube is completely or entirely accommodated in the space formed by the adapter 22 and disposable tip member 24 and thus this type larynx-stimulating member does not give any fear to the patients and can be hygienically handled by the flange.

What is claimed is:

1. A method of examining a patient to determine whether said patient is infected with *Helicobacter pylori*, which comprises steps of collecting gas in the gastric cavity of said patient, and then measuring amounts of ammonia and organic amines in the gas.

2. A method as claimed in claim 1, wherein said gas in the gastric cavity is led to the oral cavity with the aid of a vomiting reflex.

3. A method as claimed in claim 1, further comprising a step of administering to said patient at least one member selected from the group consisting of an alkaline agent, a urea preparation and hot water, prior to said collecting gas.

4. A method as claimed in claim 1, wherein said measuring is conducted at least one time before and after a vomiting reflex to obtain at least two measurements, and determining the difference in results of said measurements.

5. A method as claimed in claim 1, wherein said measuring is conducted at least one time after a vomiting reflex.

* * * * *